United States Patent [19]

Froehlich

[11] 4,321,002
[45] Mar. 23, 1982

[54] MEDICAL STAPLING DEVICE

[75] Inventor: Harold E. Froehlich, St. Anthony, Minn.

[73] Assignee: Minnesota Mining and Manufacturing Company, St. Paul, Minn.

[21] Appl. No.: 78,602

[22] Filed: Sep. 24, 1979

Related U.S. Application Data

[62] Division of Ser. No. 890,682, Mar. 27, 1978, Pat. No. 4,185,762.

[51] Int. Cl.³ .................... F15B 15/00; A43B 23/20
[52] U.S. Cl. ............................ 411/457; 206/339; 227/19
[58] Field of Search ............ 206/339; 227/19; 85/49, 85/14; 411/457

[56] References Cited

U.S. PATENT DOCUMENTS

| | | | |
|---|---|---|---|
| 2,008,086 | 7/1935 | Sorenson | 85/49 |
| 2,142,782 | 1/1939 | Gillette | 85/49 |
| 3,077,812 | 2/1963 | Dietrich | 85/49 |
| 3,218,700 | 11/1965 | Klaws | 85/49 |
| 4,014,492 | 3/1977 | Rothfuss | 227/19 |
| 4,127,227 | 11/1978 | Green | 85/49 |

FOREIGN PATENT DOCUMENTS

| | | |
|---|---|---|
| 428552 | 5/1935 | United Kingdom . |
| 442195 | 2/1936 | United Kingdom . |
| 864210 | 3/1957 | United Kingdom . |
| 784810 | 10/1957 | United Kingdom . |
| 1042384 | 9/1966 | United Kingdom . |

*Primary Examiner*—William T. Dixson, Jr.
*Attorney, Agent, or Firm*—Cruzan Alexander; Donald M. Sell; William L. Huebsch

[57] ABSTRACT

A medical stapling device in which open staples are moved along a track between two grooved rails by a drive member having spaced lugs. Upon activation of the device, the lugs are moved into engagement with the staples and advance them along the track so that the leading staple will be formed around an anvil at the end of the track and can suture living tissue adjacent the anvil. The portions of the staple that enter the tissue are smoothly curved so that they will enter like a surgeon's needle and provide a predetermined amount of gathering of the tissues, and the closed staple is shaped so that its maximum inner dimension is parallel to its central portion to restrict rotation of the staple due to tension across the suture.

2 Claims, 15 Drawing Figures

MEDICAL STAPLING DEVICE

This is a division of application Ser. No. 890,682 filed Mar. 27, 1978 U.S. Pat. No. 4,185,762.

BACKGROUND OF THE INVENTION

The present invention relates to medical stapling devices for applying metal staples to suture living tissue such a disunited skin or fascia.

The prior art is replete with medical stapling devices for use in suturing living tissues. U.S. Pat. Nos. 3,643,851; 3,662,939; 3,837,555; 3,873,016; and 4,014,492 are illustrative of such devices which include means which may be operated to move a plurality of open staples along a track and sequentially into engagement with an anvil so that the staple engaging the anvil will be closed to engage it with tissues adjacent the anvil.

Typically, such stapling devices are rather complex and apply a staple which is rectangular or square in shape after application. Such staples may be applied in different ways.

One way involves manually pulling together and everting (tenting) the edges of tissue (e.g. skin or fascia) to be joined, placing the anvil of the stapling device transverse of the juncture between the tissues, and activating the device to apply a staple. The applied staple has a straight central portion (which contacted the anvil) extending across the juncture of the tissues, straight side portions of the staple on either end of its central portion extending along the outer surfaces of the tissue and at right angles to the central portion of the staple, and generally aligned pointed end portions piercing the tissue and extending toward each other from the ends of the straight portions opposite the central portion.

Another way involves bringing the anvil and separated sharp end portions of an open staple into contact with the surfaces of tissues to be joined while the surfaces of the tissue are co-planar, and then activating the device so that the end portions of the staple enter the tissues and pull them together as the staple is closed.

Subsequent to at least partial healing of the tissues, these staples are removed by using a tool to bend the central portion of each staple to a U-shaped configuration, which bending causes the pointed end portions of the staple to separate.

Such stapling of living tissues has presented certain problems. First the open staples are pre-bent at right angles between their side and end portions. When the staple is used to join tissues with co-planar surfaces in the manner described above, these sharply bent portions of the staple must enter the tissue, which can cause tearing of the tissue adjacent the points of entry. Also, either manner of stapling with such staples results in excessive gathering of the tissues to be joined which is not recommended by some experts in the healing art (e.g. by "gathering" we mean pressing together adjacent portions of the tissues to be joined, and by "excessive gathering" we mean pressing together more of those adjacent tissue portions than is required to keep those tissues in contact adjacent and between the staples when a moderate tension is applied across the suture).

After the staples are applied, the healing tissues swell around the staples and enclose significant portions of the side portions of the staples. When the staples are then removed by bending their central portions, their L-shaped side and end portions tend to painfully tear or stretch the joined tissues as they are withdrawn.

Also, tension across the juncture between the tissues can cause some of the applied staples to rotate until the tissues are retained between their opposite corners. Swelling of the tissues around such a rotated staple can obfuscate its orientation so that a person removing the staple may inadvertently bend one of its side portions (instead of its central portion) to a generally U-shaped configuration. This can cause its opposite side and end portion to significantly tear tissues and cause pain as the staple is removed.

SUMMARY OF THE INVENTION

The present invention provides a mechanically simple medical stapling device which inserts a metal staple having a shape adapted to enter living tissues with a minimum of tissue damage, to gather joined tissues by a predetermined amount that will just maintain the tissues in contact when a moderate tension is applied across the suture, to provide a closed staple that will not tend to rotate within the tissues, and to allow the ends of the staple to be withdrawn from swelled healing tissue with minimum damage to the tissue by bending its central portion in the manner described above.

The stapling device is of the type including a frame, an anvil mounted in a fixed position relative to the frame, and means for moving a plurality of open staples along a track and sequentially into engagement with the anvil to close the staple engaging the anvil. In the improved stapling device according to the present invention, however, the means for moving the staples comprises a driver mounted on the frame for movement along a predetermined path generally aligned with the track between first and second positions with the driver more closely adjacent the anvil in its second position; a staple engaging member comprising a plurality of spaced lugs adapted to engage staples along the track; and means for mounting the staple engaging member to cause movement thereof from an initial position with its lugs spaced from staples along the track toward the track to an engage position with the lugs aligned with staples along the track during a first position of movement of the driver from its first toward its second position; to cause movement of the staple engaging member with the driver and along the track to move the staples and engage the leading staple with the anvil during a second portion of its movement toward the second position; to cause movement of the lugs away from the track and out of engagement with staples along the track during a first position of movement of the driver from its second position back toward its first position; and to cause movement of the staple engaging member with the driver back to its initial position during a second portion of the movement of the driver back toward its first position.

Preferably to open wire staples used in he stapler comprise a generally U-shaped central portion having at least one arcuate part; and smoothly curved outer portions terminating in sharp points with successive parts of its outer portions starting from its central portion being at increasingly greater distances from the adjacent arcuate part of the central portion. When the staple is closed by bending the arcuate part of the central portion adjacent each of its curved outer portions, its curved outer portions can enter and smoothly gather tissues in the manner of a surgeon's needle to produce minimum damage to the tissues being sutured. Also, the shape of its generally U-shaped central portion and each of its curved portions are such that when the adjacent arcuate part of the central portion is essentially straightened to close the staple, the maximum inside dimension of the closed staple will be parallel to its straightened arcuate part. This restricts the tendency for the closed staple to rotate due to tension across the juncture between the tissues. Upon removal its central portion will be engaged and bent, whereupon the curved end portions will retract with minmum damage to the tissues and pain to the patient.

Also preferably staples to be used in the stapler assembly are loaded into a cartridge which may be releasably mounted on the frame of the stapler. The cartridge includes portions defining the track for the staples, which portions comprise parallel elongate rails having opposed parallel grooves. A plurality of the staples have the outermost portions of their arcuate end portions in the grooves and are frictionally engaged between the rails with the points of the staples pointing toward a first end of the cartridge; and are disposed in closely adjacent relationship along the grooves. The cartridge is open along one side of the rails to afford access to the staples along the track, by the spaced lugs on the staple engaging member so that the lugs can move between the staples and drive the staples along the track and sequentially into engagement with the anvil on the stapler assembly which is aligned with the track at the first end of the mounted cartridge.

BRIEF DESCRIPTION OF THE DRAWING

The present invention will be further described with reference to the accompanying drawing where like numbers refer to like parts in the several views, and wherein.

DESCRIPTION OF THE PREFERRED EMBODIMENT

Figure 1:
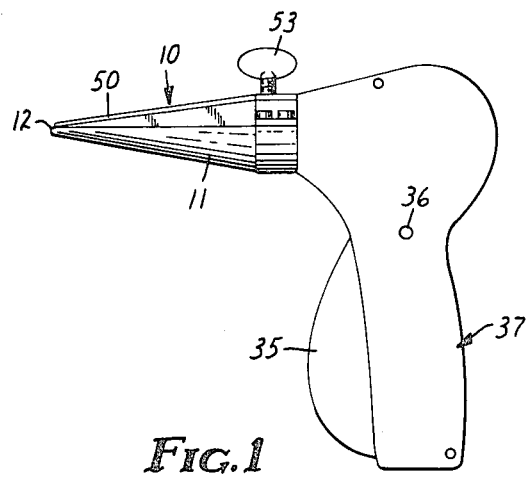
FIG. 1 is a side view of a stapling device according to the present invention.

Referring now to the drawing there is shown a stapling device or stapler according to the present invention, generally designated by the numeral 10. The stapling device 10 includes a frame 11, an anvil 12 mounted on the frame 11, and means for moving a plurality of open staples 13 along a track 14 and sequentially into engagement with the anvil 12 (FIG. 11) to close the staple 13 engaging the anvil 12 (FIG. 12) so that the staple 13 may suture living tissues 16 (such a disunited skin or fascia) adjacent the anvil 12.

As is best seen in FIGS. 3 through 7, the means for moving the open staples along the track 14 includes a driver 18 mounted on the frame 11 for movement along a predetermined path generally aligned with the track between a first position (FIG. 3) and a second position (FIG. 5) with the driver 18 more closely adjacent the anvil 12 in its second position. Also included is a staple engaging member 19 comprising a plurality of spaced lugs 20 adapted to engage staples 13 along the track 14. The staple engaging member 19 is mounted by means for causing movement thereof from an initial position (FIG. 3) with its lugs 20 spaced from staples 13 along the track 14 toward the track 14 to an engage position (FIG. 4) with the lugs 20 aligned with and between the staples 13 along the track 14 during a first position of movement of the driver 18 from its first toward its second position; for causing movement of the staple engaging member 19 with the driver 18 to engage and move staples 13 along the track 14 and to close the leading staple 13 along the track 14 around the anvil 12 during a second portion of the movement of the driver toward its second position (FIGS. 5 and 12); for causing movement of the lugs 20 away from the track 14 and out of engagement with the staples 13 along the track 14 during a first position of movement of the driver 18 from its second position (FIG. 5) back toward its first position; and to move the staple engaging member 19 with the driver 18 back to its initial position (FIG. 3) during a second portion of movement of the driver 18 back toward its first position.

The driver 18 comprises an elongate driving portion 22 which has a semi-cylindrical bearing surface 23 (FIGS. 6 and 7) and a longitudinally extending U-shaped slot 24 along its side opposite its bearing surface 23 so that the driving portion 22 is generally C-shaped in cross section. Its bearing surface 23 is slidably mounted against a mating bearing surface 25 on the frame 11 for movement toward and away from the anvil 12. The driver 18 also includes a stepped cylindrical driven portion (see FIGS. 3, 4 and 5) fixed on the end of the driving portion 22 opposite the anvil 12 and having an axis aligned with the direction of sliding movement for the driver 18. The driving portion includes three cylindrical portions 27, 28 and 29 coaxially fixed to and spaced by a cylindrical rod 30. The cylindrical front portion 27 attaches the rod 30 to the driving portion 22. The center cylindrical portion 28 retains a compression spring 31 within a chamber in the frame 11 and between itself and a collar 32 fixed to the frame 11 to provide means for biasing the driver 18 to its first position. The portion of the rod 30 between the center and rear cylindrical portions 28 and 29 is slidably mounted in a bearing 33 on the frame 11 to provide, with the cylindrical bearing surfaces 23 and 25, the means for slidably mounting the driver 18 on the frame 11.

The rear cylindrical portion 29 is fixed on the end of the rod 30 and is concave on its side opposite the rod 30. An actuating trigger 35 is pivotably mounted by a pin 36 on a handle assembly 37 and has a knob 34 at one end adapted to engage the concave surface of the rear cylindrical portion 29, and a portion projecting from the handle assembly 37. When the projecting portion of the trigger is manually squeezed into the handle assembly 37, the knob 34 will engage and move the driver 18 to its second position so that one of the staples 13 will be applied.

Figure 2:
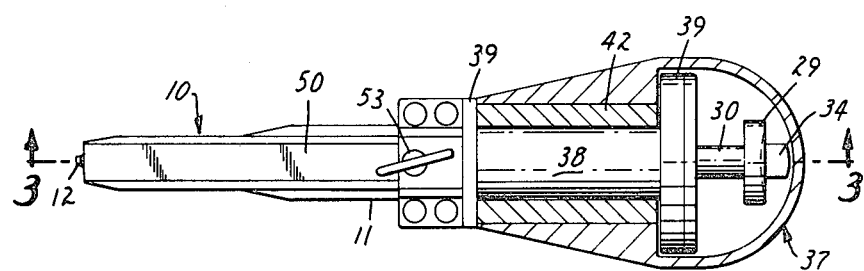
FIG. 2 is an enlarged top view of the stapling device of FIG. 1 having parts broken away to show details.
Figure 3:
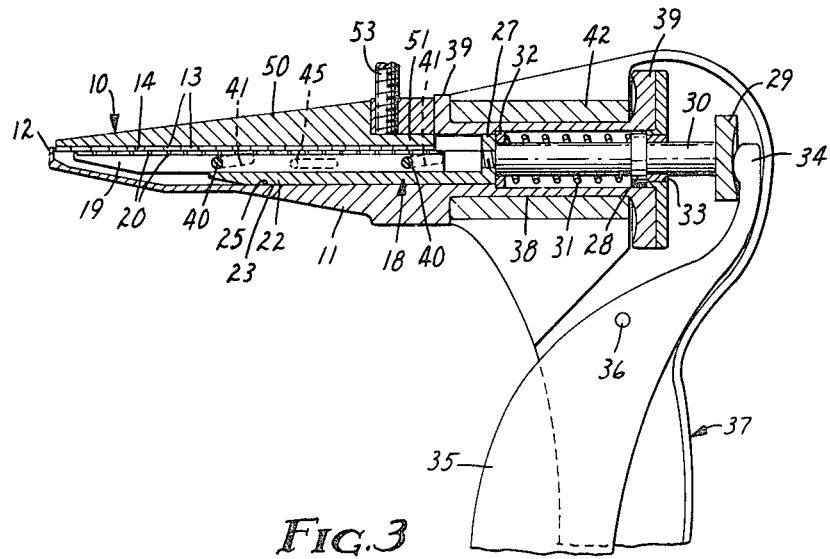
FIG. 3 is a sectional view taken approximately along the line 3—3 of FIG. 2 and showing a normal position of a staple driving mechanism in the stapling device.
Figure 4:
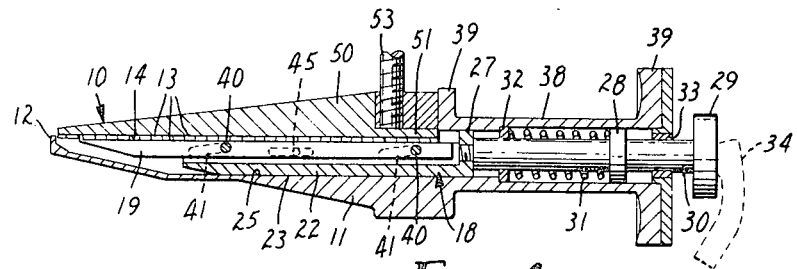
FIGS. 4 and 5 are fragmentary sectional views taken approximately along the line 3—3 of FIG. 2 which show sequential positions into which the staple driving mechanism is moved during the application of a staple.
Figure 5:
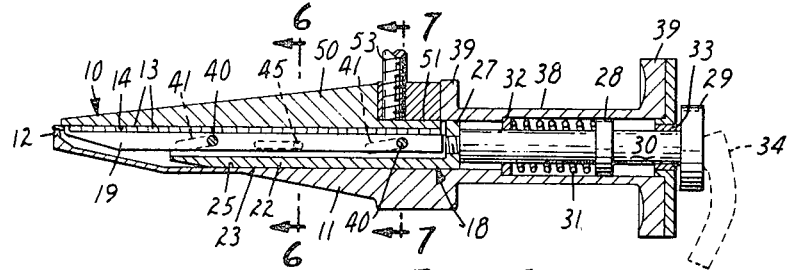
Figure 8:
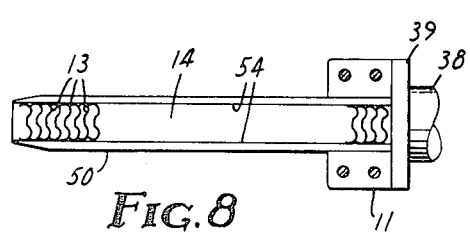
FIG. 8 is a fragmentary sectional view taken approximately along line 8—8 of FIG. 6.

The frame 11 on which the driver 18, staple engaging member 19 and anvil 12 are mounted is rotatable relative to the handle assembly 37 to afford various orientations of the width of the staple relative to the hand of a user grasping the handle assembly 37. This, together with the long tapered outline of the stapling device 10 toward the anvil 12 which allows excellent visibility of the tissue being sutured, affords great versatility in use of the stapling device 10. As is seen in FIGS. 2 and 3, the frame 11 has a cylindrical surface 38 between spaced flanges 39 and the handle assembly 37 includes a cylindrical bearing 42 adapted to engage that cylindrical surface 38 so that the frame 11 may be rotated to change the orientation of the dispensed staple; the knob 34 of the trigger 35 being adapted to engage the concave surface of the cylindrical portion 29 at any relative orientation therebetween so that the stapling device 10 may be activated.

If desired, the handle assembly 37 can be removed, and the stapling device 10 can be activated by manual pressure applied directly to the cylindrical portion 29.

The staple engaging member 19 is elongate and generally rectangular in cross section with two spaced parallel rows of spaced lugs 20 along one of its surfaces. it is slidably received in the slot 24 in the drive portion 22 with the lugs 20 exposed to allow both relative longitudinal sliding movement between the driver 18 and the staple engaging member 19, and sliding movement of the staple engaging member 19 into and out of the slot 24 in a direction normal to its elongate axis so that the lugs 20 can move toward and away from the track 14 along which the staples 13 are spaced.

Figure 7:
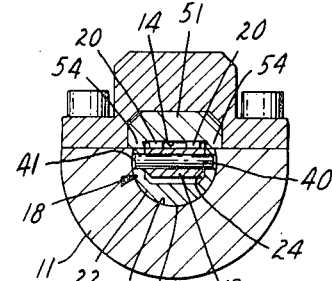

The staple engaging member 19 includes two parallel pins 40 extending transversely to the axes of the bearing surfaces 23 and 25, and engaging cam slots 41 in the driving portion 22 which guide and limit relative movement between the driver 18 and staple engaging member 19. The surfaces defining the slots 41 are inclined to cause movement of the staple engaging member 19 out of the slot 24 (with its axis parallel to that of the driver 18) to a position with the lugs 20 between staples 13 along the track 14 as the staple engaging member 19 is moved toward the anvil 12 relative to the driver 18; and conversely to cause movement of the staple engaging member 19 into the slot 24 with the lugs 20 spaced from staples 13 along the track 14 as the staple engaging member 19 is moved away from the anvil 12 relative to the driver 18. Means for frictionally retarding movement of the staple engaging member 19 with respect to the frame 11 are provided by two opposed friction assemblies 43 (FIG. 7). Each friction assembly 45 includes a housing 46 threadably mounted in the frame 11 and extending through a clearance opening in the driving portion 22 of the driver 18, a spring 47, and a ball 48 which is pressed by the spring 47 into frictional engagement with one side of the staple engaging member 19. Such frictional engagement is adjusted to prevent longitudinal movement of the staple member 19 with the driver 18 until the pins 40 contact the trailing ends of the slots 41. Thus with the pins 40 initially located at the leading ends of the slots 41 (so that the lugs 20 are spaced from the staples 13 along the track 14) and with the driver 18 in its first position (FIG. 3), movement of the driver 18 toward its second position will first cause movement of the staple engaging member 19 at a right angle to its axis to its engage position by camming engagement between the pins 40 and the walls defining the slots 41 as the walls defining the slots 41 move toward the anvil 12 relative to the pins 40, and will then cause movement of the staple engaging member 19 with the driver 18 during a second portion of the movement of the driver 18 toward its second position after the trailing ends of the slots 41 engage the pins 40. Subsequently upon movement of the driver 18 from its second position back toward its first position under the influence of the spring 35, the walls defining the slots 41 will first move along the pins 40, cam the staple engaging member away from the track 14, and will then carry the staple engaging member 19 back to its initial position after the trailing ends of the slots 41 engage the pins 40.

Figure 9:
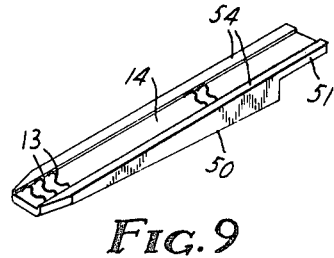
FIG. 9 is a perspective view of a replaceable staple cartridge used in the stapling device of FIG. 1.
Figure 10:
FIG. 10 is a side view of the cartridge of FIG. 9.
Figure 6:
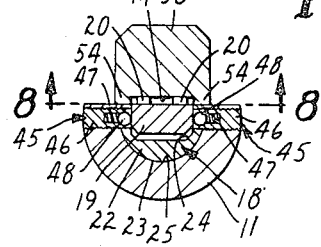
FIGS. 6 and 7 are sectional views taken respectively along lines 6—6 and 7—7 of FIG. 5.

The track 14 along which the open staples 13 are spaced is defined by an elongate cartridge 50 removably mounted on the frame 11. The cartridge 50, best seen in FIGS. 9 and 10, includes a generally rectangular projecting end portion 51 adapted to be received in a socket in the frame 11 and to be retained therein by a thumb screw 53. Also included are two parallel elongate rails 54 having opposed parallel grooves which define the track 14. The staples 13 have arcuate end portions in the grooves and frictionally engaged with the rails 54, with the staples 13 all opening toward the end of the cartridge 50 opposite its end portion 51 and being disposed in closely adjacent relationship along the grooves. The cartridge 50 is open along one side of the rails 54 to afford access by the lugs 20 on the staple engaging member 19 with the staples 13 spaced along the track 14.

Figure 11:
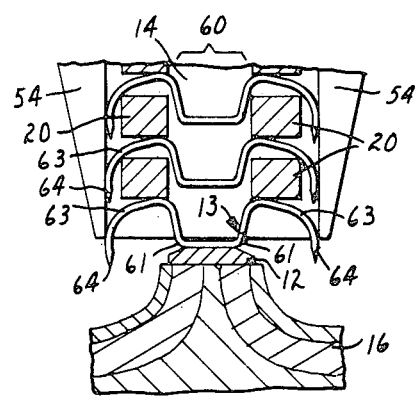
FIGS. 11 and 12 are fragmentary sectional views sequentially showing the attachment of a first embodiment of a staple applied by the stapling device of FIG. 1 to suture living tissues.
Figure 12:
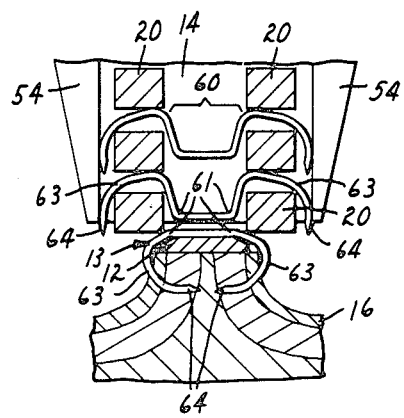

The open wire staple 13 used in the stapling device and the manner in which it is closed is best seen in FIGS. 11 and 12 which illustrate the application of one of the staples 13 to the tissue or disunited skin 16 which has been everted prior to application (as may be necessary when the flesh below the skin does not provide enough support for the skin so that the staple will enter skin disposed in a co-planar relationship). The staple 13 is formed from circular metal wire (e.g. 0.058 centimeter (0.023 inch) diameter 316L stainless steel). When open, the staple 13 consists of a generally U-shaped central portion 60 having two spaced arcuate parts 61, and two smoothly curved outer portions 63 terminating in sharp needle-like points 64. The staple is bent at an angle in the range of 75 to 90 degrees at the juncture between the portions 60 and 63 on each of its sides. When the stable 13 is open, successive parts of its outer portions 63 starting from the adjacent arcuate part 61 are at increasingly greater distances from the arcuate part 61 (when measured along straight lines between the successive parts of the curved outer portions 63 and the adjacent arcuate part 61). When the open staple 13 is closed by bending its arcuate parts 61 to a generally straight condition, the curved outer portions 63 can enter and smoothly gather tissues (such as the disunited skin 16) positioned adjacent the anvil 12. The shape of the U-shaped central portion 60, each of the curved outer portions 63 and the bends between the portions 60 and 63 are such that when the arcuate parts of the central portion 60 are generally straightened to close the staple 13 (as shown in FIG. 12), the shape of the staple 13 is generally D-shaped with the maximum dimension of the closed staple being parallel to and adjacent the straightened arcuate parts 61 to provide a desirable stability against rotation for the closed staple 13.

Figure 13:
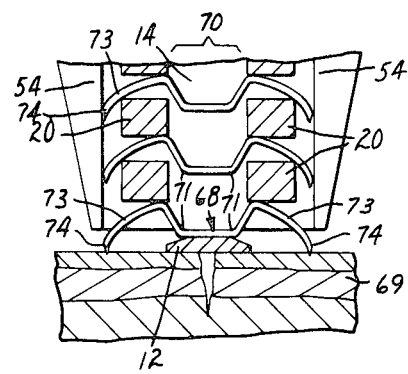
FIGS. 13, 14 and 15 are fragmentary sectional views sequentially showing the attachment of a second embodiment of a staple applied by the stapling device of FIG. 1 to suture living tissues.
Figure 14:
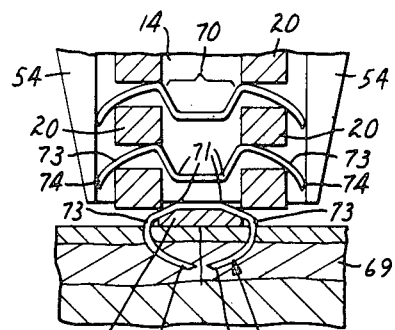
Figure 15:
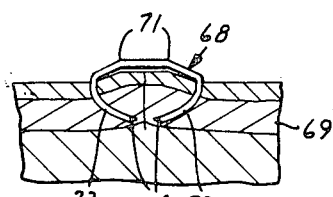

FIGS. 13, 14 and 15 illustrate an alternative embodiment of an open wire staple 68 according to the present invention as it is applied by the stapling to suture disunited skin 69 in a co-planar relationship. The device 10 will close the staple 68 to the generally D-shaped configuration shown in FIG. 15. Like staple 13, the open staple 68 includes a generally U-shaped central portion 70 having two spaced arcuate parts 71, and two smoothly curved outer portions 73 terminating in sharp points 74. The staple 68 is bent at an angle in the range of 75 to 90 degrees at the juncture between its portions 70 and 73 on each of its sides. When the staple 68 is open (FIG. 13), successive parts of its curved outer portions 73 starting from the adjacent arcuate part 71 are at increasingly greater distances from the adjacent arcate part 71 (when measured on a straight line between the successive parts of the curved outer portions 73 and the adjacent arcuate part 71). When the staple 68 is then closed by bending the arcuate parts 71 to a generally straight condition (FIG. 14), the curved outer portions 73 can enter and smoothly gather tissues (such as the disunited skin 69) positioned adjacent the anvil 12. Also the shape of the U-shaped central portion 70 and each of the curved outer portions 73 is such that when the arcuate parts 71 of the central portion 70 are generally straightened to close the staple 68, the maximum inside dimension of the closed staple 68 will be generally parallel to and adjacent a line connecting the straightened arcuate parts 71 to provide a desirable stability against rotation for the closed staple 68. To close the staple 68, the arcuate parts 71 are bent slightly beyond straight to provide a slightly raised central portion for the closed staple 68 which allows a degree of swelling for the healing tissue 69 and easy insertion of the staple removal tool.

The wire staple 68 differs from the staple 13 in that its curved outer portions 73 have a greater radius of curvature than do the curved portions 63 for the staple 13. Thus its curved portions 73 bite less deeply into the tissue 69 than do the curved portions 63 which is appropriate for joining the co-planar disunited skin 69 as opposed to everted skin 16.

It will be understood that the preferred embodiments of the stapling device 10 and staples 13 and 68 disclosed herein may be subject to many modifications and alterations without departing from the scope of the invention which is defined by the claims. For example the anvil 12 could be mounted on the frame of the stapler or on a removable cartridge which for purposes of the claims could be considered a part of the frame. Also the pair of lugs 20 at the distal end of the staple engaging member 19 may be notched to partially receive the curved portions 63 or 73 of the staple being closed to insure that the staple will stay in alignment with the tracks 14 as it is bent.

I claim:

1. An open wire staple for suturing living tissue, said open staple comprising a generally U-shaped central portion having at least one arcuate part; and outer portions terminating in sharp points, said outer portions being smoothly curved from said sharp points to adjacent said central portion with successive parts of said curved outer portions starting from adjacent said central portion being at increasingly greater distances from the adjacent arcuate part of said central portion, said staple is closed by bending generally straight the arcuate part of said central portion adjacent each of said curved outer portions so that said curved outer portions can smoothly enter and gather living tissue, during such closure the sharp points on the outer portions will move to positions with their sharp points adjacent and generally aligned with each other to provide a generally D-shaped closed staple with the maximum inside dimension of the closed staple generally parallel to said central portion, and the central portion of the closed staple can subsequently be bent to smoothly retract the smoothly curved outer portions of the staple from the living tissue.

2. An open wire staple for suturing living tissue according to claim 6 wherein the U-shaped portion of said staple has two spaced arcuate parts, and said staple is bent at an angle in the range of 75 to 90 degrees between said central and outer portions on each side of said staple.

* * * * *

UNITED STATES PATENT AND TRADEMARK OFFICE
CERTIFICATE OF CORRECTION

PATENT NO. : 4,321,002
DATED : March 23, 1982
INVENTOR(S) : Harold E. Froehlich

It is certified that error appears in the above—identified patent and that said Letters Patent is hereby corrected as shown below:

Col. 1, line 10, "a" should read --as--.
Col. 2, line 55, "to" should read --the--.
Col. 2, line 55, "he" should read --the--.
Col. 3, line 8, "minmum" should read --minimum--.
Col. 5, line 27, "it" should read --It--.
Col. 6, line 11, insert before "cam" --to--.
Col. 7, line 1, after "stapling" insert --device 10--.
Col. 7, line 13, "arcate" should read --arcuate--.

Signed and Sealed this

Twenty-sixth Day of February 1985

[SEAL]

*Attest:*

DONALD J. QUIGG

*Attesting Officer*  *Acting Commissioner of Patents and Trademarks*